United States Patent [19]
Schmieding et al.

[11] Patent Number: 5,690,677
[45] Date of Patent: Nov. 25, 1997

[54] METHOD FOR INSTALLING A SUTURE ANCHOR THROUGH A CANNULATED TISSUE-SHIFTING GUIDE

[75] Inventors: Reinhold Schmieding, Naples, Fla.; Stefan Krupp, Munich, Germany

[73] Assignee: Arthrex, Inc., Naples, Fla.

[21] Appl. No.: 604,611

[22] Filed: Feb. 21, 1996

Related U.S. Application Data

[63] Continuation-in-part of Ser. No. 552,694, Nov. 3, 1995, which is a continuation of Ser. No. 197,829, Feb. 17, 1994, Pat. No. 5,466,243.

[51] Int. Cl.$^6$ ................................................ A61B 17/00
[52] U.S. Cl. ................................. 606/232; 606/104
[58] Field of Search .............................. 606/232, 139, 606/148, 151, 222–223, 72, 73, 75, 104

[56] References Cited

U.S. PATENT DOCUMENTS

| | | | |
|---|---|---|---|
| 5,041,129 | 8/1991 | Hayhurst et al. | 606/151 |
| 5,064,411 | 11/1991 | Gordon, III | 606/222 |
| 5,370,661 | 12/1994 | Branch | 606/232 |
| 5,458,608 | 10/1995 | Wortrich | 606/232 |
| 5,470,337 | 11/1995 | Moss | 606/232 |

*Primary Examiner*—Jeffrey A. Schmidt
*Attorney, Agent, or Firm*—Ostrolenk, Faber, Gerb & Soffen, LLP

[57] ABSTRACT

An arthroscopic method and apparatus for implanting a suture anchor into tissue using a cannulated tissue-shifting guide. Tissue at a repair site is secured with a cannulated tissue-shifting guide. Suture material is appended to a suture anchor. The suture anchor is attached to a device driver and installed through the cannulated tissue-shifting guide at the repair site and into bone. A power drill can be attached to the device driver and used to drive the suture anchor during installation.

11 Claims, 3 Drawing Sheets

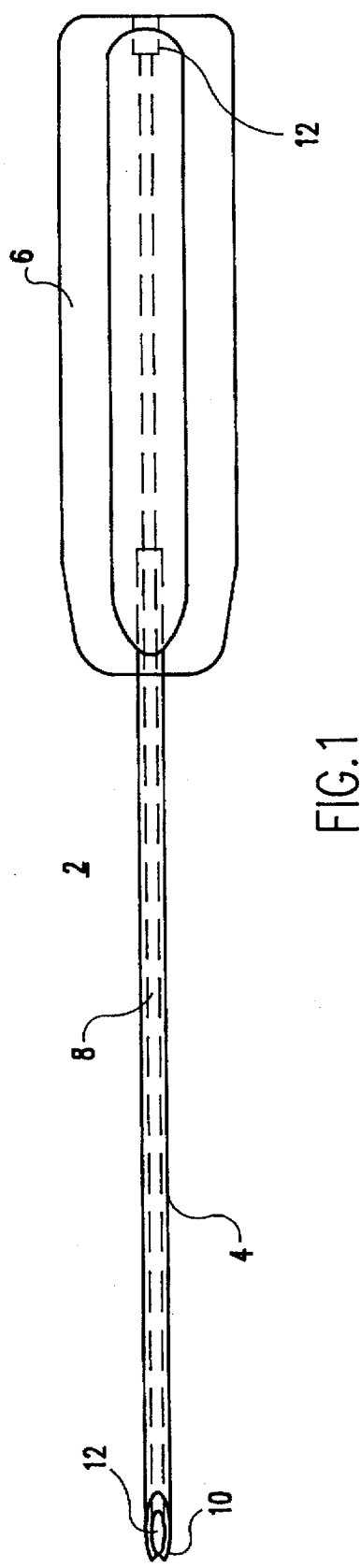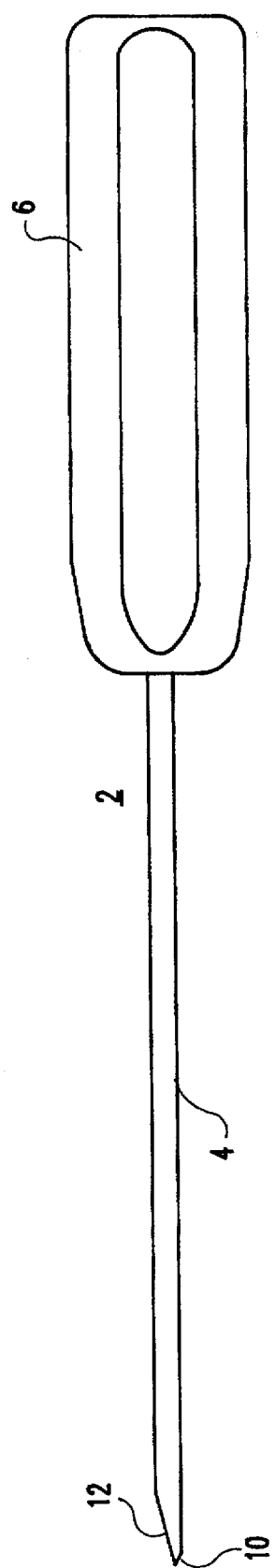

METHOD FOR INSTALLING A SUTURE ANCHOR THROUGH A CANNULATED TISSUE-SHIFTING GUIDE

This is a continuation-in-part of application Ser. No. 08/552,694, filed Nov. 3, 1995, which is a continuation of application Ser. No. 08/197,829, filed Feb. 17, 1994, now U.S. Pat. No. 5,466,243, the disclosures of which are incorporated herein by reference.

BACKGROUND OF THE INVENTION

1. Field of the Invention

The present invention relates to an arthroscopic surgical method and apparatus for suture fixation and, more specifically, to an arthroscopic method and apparatus for installing a suture anchor through a cannulated tissue-shifting guide.

2. Brief Description of the Prior Art

Suture anchors are used in arthroscopic surgery to secure suture material to tissue. Various suture anchor assemblies have been developed. For example, U.S. Pat. Nos. 4,632,100 to Somers et al. and 4,898,156 to Gatturna et al. disclose suture anchors and tools for suture anchor installation. See also U.S. Pat. No. 4,899,743 to Nicholson et al.

The devices of the above-mentioned patents are disadvantageous because they do not secure the anchor-delivering end of the driver at the tissue repair site while the suture anchor is driven into the repair tissue. In addition, the devices do not facilitate repositioning and securing the tissue at the repair site in preparation for insertion of the suture anchor.

In order to provide stabilization at the tissue repair site, many of the prior art devices require that the suture anchor be inserted into a pre-drilled hole, as in Gatturna et al. and Nicholson et al. Other prior art devices, such as the device taught by Somers, rely on the technical skill of the surgeon to screw, for example, a self-tapping suture anchor into bone.

Guiding small suture anchor pins while accurately positioning repair tissue and driving the anchor pins into bone can be excessively demanding, particularly, for example, in arthroscopic Bankart repair. Inserting suture anchors into the glenoid rim is technically formidable, making the procedure infeasible.

SUMMARY OF THE INVENTION

The present invention overcomes the above-noted disadvantages by providing a method and apparatus for installing a suture anchor through a cannulated tissue-shifting guide. The guide has a guide tip that preferably is forked or V-shaped and is used to shift and secure tissue at the installation site, providing a sturdy guide-way through which suture anchors and other appliances can be delivered to a tissue repair site for implantation.

The method of the present invention for installing a suture anchor includes the steps of shifting tissue with a forked, cannulated tissue-shifting guide and introducing a threaded suture anchor to the tissue through the cannulated tissue-shifting guide. Once the suture anchor is implanted, the cannulated tissue-shifting guide is removed, leaving the suture anchor in place.

The depth of implantation can be controlled with a depth gauge or drill stop device. The method is repeated to effect further suture anchor installations.

By the method of the present invention, arthroscopic implantation of suture anchors is made simpler and more feasible due to increased stability at the tissue repair site during installation.

Other features and advantages of the present invention will become apparent from the following description of the invention which refers to the accompanying drawings.

BRIEF DESCRIPTION OF THE DRAWINGS

FIG. 1 is a top view of the cannulated tissue-shifting guide device of the present invention.

FIG. 2 is a side elevation of the cannulated tissue-shifting guide device of the present invention.

DETAILED DESCRIPTION OF THE PREFERRED EMBODIMENT

Figure 3:
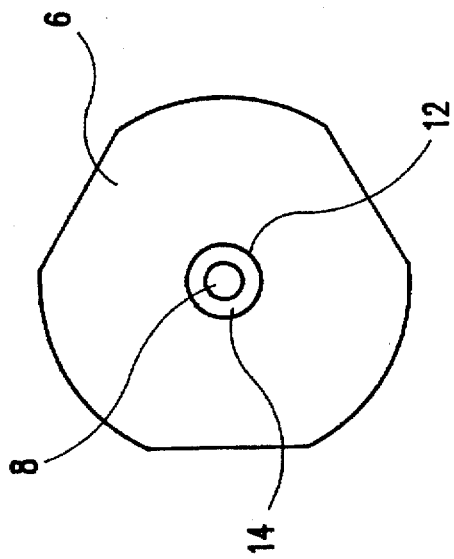
FIG. 3 is an end view of the tissue-shifting guide of the present invention.

Referring to FIGS. 1 and 2, the present invention relates to a cannulated tissue-shifting guide 2 consisting of a cannulated shaft 4 secured to an aluminum handle 6.

Guide 2 has a central cannula 8 that extends through shaft 4 and handle 6 for receiving a suture anchor driver, as described in more detail below. A V-shaped guide or forked tip 10 and an open side window 12 are formed on the distal end of shaft 4.

As shown in FIG. 3, handle 4 has a comfortable, three-sided grip and includes a hollow bushing 12 that is press fit into the proximal end of handle 6. Bushing 12 includes a chamfer 14 to assist in alignment of the suture anchor and suture driver during insertion into the guide.

Cannulated shaft 4 also is chamfered at the proximal end, which is embedded in handle 6. The chamfer on shaft 4 similarly assists in alignment and insertion of the suture driver and suture anchor received within the guide.

Figure 4:
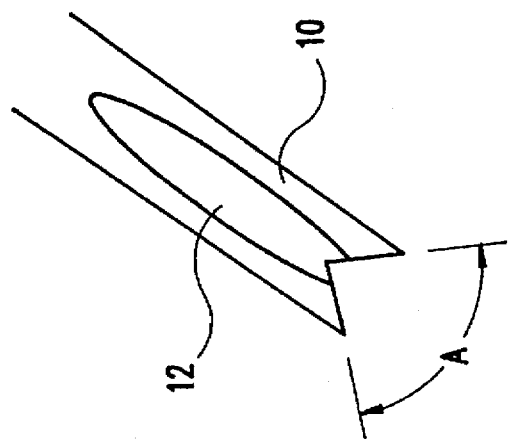
FIG. 4 is an enlarged view of the forked tip of the guide of the present invention.

FIG. 4 is an enlarged view of forked tip 10. As shown in FIG. 4 the V-shaped tip 10 is formed by a notch having an angle A of preferably 80 degrees. The V-shaped configuration of the guide tip sits precisely onto the rim of the glenoid for accurate, anatomical screw placement.

Figure 5:
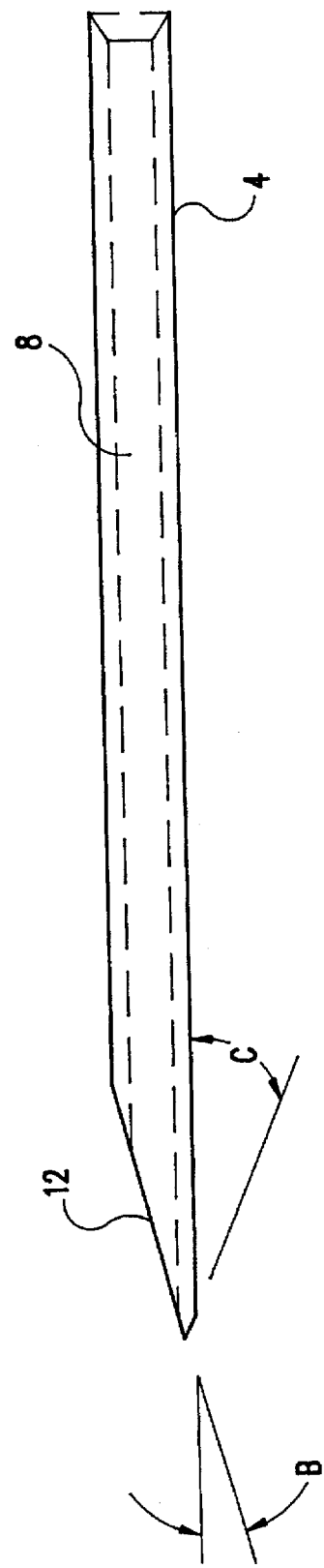
FIG. 5 is a detail view of the shaft of the guide of the present invention.

Referring also to FIG. 5, window 12 is formed by a surface cutting across the cannulated shaft at an angle B of preferably 15 degrees. The forked tip 10 is pointed for securing tissue at the repair site. The points are further sharpened by formation of another surface cutting through the cannulated shaft at an angle C.

Figure 6:
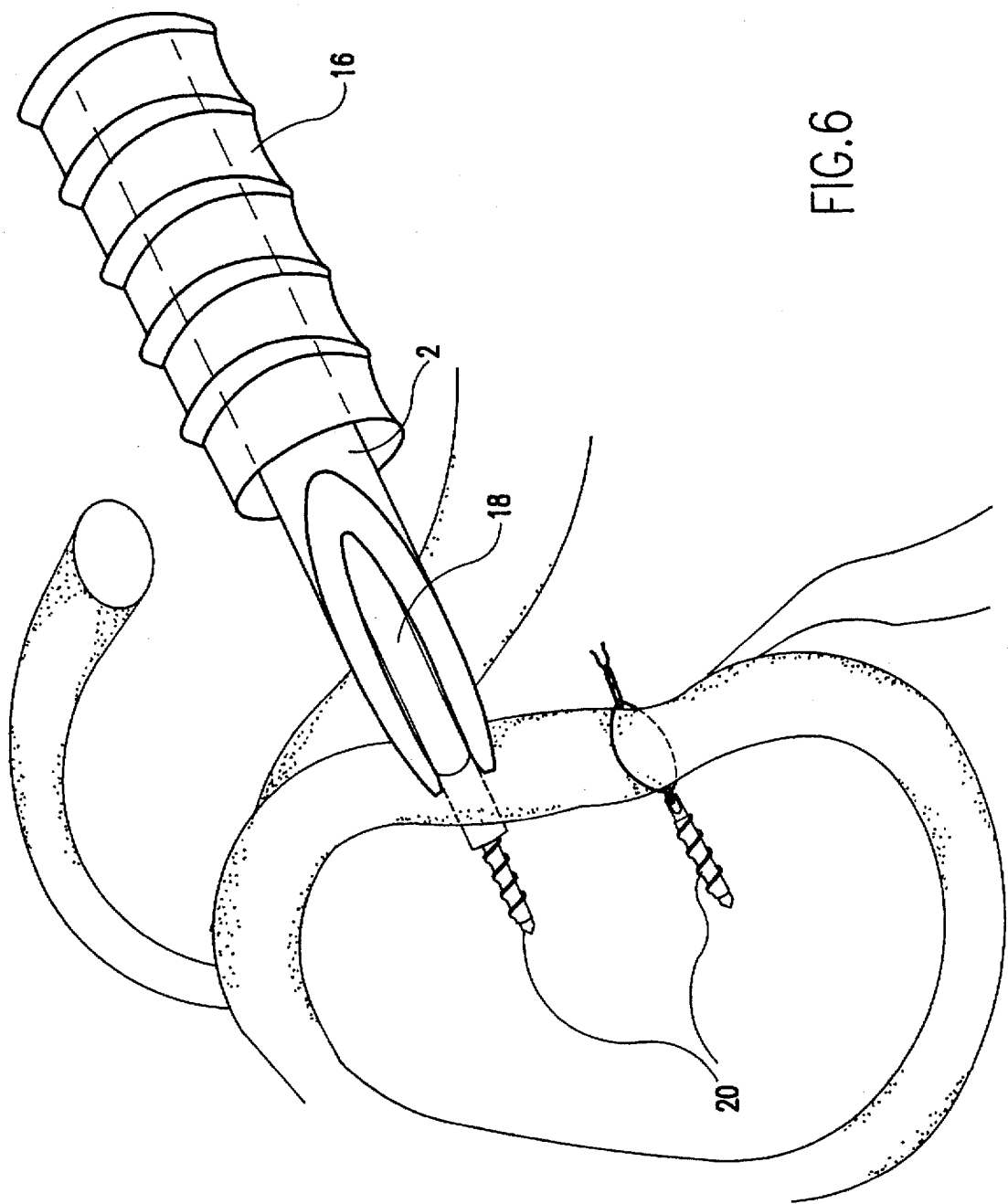
FIG. 6 is a perspective view of a suture anchor being installed using the guide of the present invention.

Referring to FIG. 6, the method of installing suture anchors in accordance with the present invention is shown. The tissue-shifting guide 2 is held in one hand using handle 6 and is inserted through a cannulated portal 16 into the surgical site, approaching the area to be repaired with forked tip 10. The tissue into or through which a suture anchor is to be inserted is engaged with the sharp points of tip 10, which bite into the tissue to assist in positioning and securing.

The tissue is shifted and held in place as necessary, and a suture anchor driver 18 (shown in greater detail in U.S. Pat. No. 5,466,243) loaded with a threaded suture anchor 20 is passed through bushing 12 and the cannula 8. As the suture anchor approaches the distal end of guide 2, the anchor will become visible, as viewed with an endoscope, for example, through window 12.

To thread the suture anchor prior to insertion, appropriately sized suture is threaded through an eye of the suture anchor. The eye and drive end of suture anchor 20 are seated in device driver 18. A threading device such as shown in U.S. Pat. No. 5,466,243 may be used to thread the suture through the device driver.

When device driver 18 is fully inserted, the suture anchor 20 at the distal end thereof projects out through the end of the cannulated shaft 4 and beyond the forked tip 10 into position at the tissue repair site. A power drill is attached to the proximal end of the driver. The suture anchor 20 has a threaded body as shown in FIG. 6, and is installed into the tissue, (e.g., the glenoid rim) in one maneuver by activating the power drill to rotate and advance the suture anchor. An adjustable drill depth guide stop can provide insertion depth control.

Preferably, a mark is formed on the proximal end of the inserter to correspond with the end of the suture anchor eyelet for direct visualization of insertion depth during arthroscopic and open procedures done in conjunction with the guide of the present invention.

Once suture anchor 20 is in place, device driver 18 and cannulated tissue-shifting guide 2 are withdrawn from the repair site. The threaded suture anchor 20 is left in place for continuing the repair. Knots in the suture material may be tied using a knot pusher such as that described in U.S. Pat. No. 5,176,691. The installation procedure is repeated as necessary to install additional suture anchors. Tissue may be subsequently secured with free needles using standard open Bankart repair techniques.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for installing a suture anchor for securing tissue to bone using a cannulated tissue-shifting guide having a tip, the method comprising the steps of:
   (a) contacting the tissue with the tip of the cannulated tissue-shifting guide;
   (b) introducing the suture anchor to the tissue through the cannulated tissue-shifting guide;
   (c) installing the suture anchor through the tissue and into the bone by rotating and advancing the suture anchor; and
   (d) removing the cannulated tissue-shifting guide from the repair site, leaving the suture anchor installed in the bone.

2. The method of claim 1, wherein the step of installing the suture anchor comprises using a power drill to rotate and advance the suture anchor into the bone.

3. The method of claim 1, further comprising the step of threading the suture anchor with suture prior to the step of introducing the suture anchor to the tissue.

4. The method of claim 1, further comprising the step of delivering the cannulated tissue-shifting guide to the tissue through a portal.

5. The method of claim 1, wherein the step of contacting the tissue with the tip of the cannulated tissue-shifting guide comprises maneuvering the guide using a handle disposed on the proximal end of the cannulated guide.

6. The method of claim 1, wherein the tip of the cannulated tissue-shifting guide comprises a protrusion, and the step of contacting the tissue with the tip of the cannulated tissue-shifting guide comprises contacting the tissue with the protrusion.

7. The method of claim 6, wherein the protrusion is forked, and the step of contacting the tissue with the tip of the cannulated tissue-shifting guide comprises contacting the tissue with the forked protrusion.

8. The method of claim 1, wherein the cannulated guide further comprises an opening in a wall of the guide, and the step of introducing the suture anchor to the tissue through the cannulated tissue-shifting guide comprises viewing the suture anchor being passed through the cannulated tube through the opening in the wall of the guide.

9. A method of installing a suture anchor into bone using a cannulated tissue-shifting guide having a tip, the suture anchor having a proximal end, the method comprising the steps of:
   (a) coupling the proximal end of the suture anchor to a device driver;
   (b) threading the suture from the suture anchor through the device driver;
   (c) inserting the device driver and the suture anchor through the cannulated tissue-shifting guide;
   (d) attaching a power drill to the proximal end of the device driver; and
   (e) installing the suture anchor into the bone using the power drill to rotate and advance the suture anchor.

10. The method of claim 9, further comprising the steps of:
   contacting the tissue with the tip of the cannulated tissue-shifting guide; and
   positioning the tissue with the cannulated tissue-shifting guide.

11. The method of claim 10, wherein the steps of contacting and positioning the tissue comprise maneuvering the tissue-shifting guide using a handle disposed on a proximal end of the guide.

* * * * *